United States Patent

Crawley et al.

[11] Patent Number: 5,217,977
[45] Date of Patent: Jun. 8, 1993

[54] HETEROCYCLIC CYCLOALKANES

[75] Inventors: Graham C. Crawley, Macclesfield, United Kingdom; Jean-Marc M. M. Girodeau, Rilly la Montagne, France

[73] Assignees: Imperial Chemical Industries PLC, London, England; ICI Pharma, Cergy Cedex, France

[21] Appl. No.: 793,330

[22] Filed: Nov. 15, 1991

Related U.S. Application Data

[63] Continuation of Ser. No. 485,492, Feb. 27, 1990, abandoned.

[30] Foreign Application Priority Data

Feb. 28, 1989 [EP] European Pat. Off. ......... 894005594

[51] Int. Cl.$^5$ .................. C07D 215/22; C07D 213/30; A61K 31/47; A61K 31/44
[52] U.S. Cl. .................... 514/311; 514/312; 514/313; 514/314; 546/153; 546/156; 546/157; 546/158; 546/164; 546/165; 546/172; 546/174; 546/175; 546/178; 546/179
[58] Field of Search ............... 514/311, 312, 313, 314; 546/156, 157, 158, 164, 165, 172, 174, 175, 178, 179, 153

[56] References Cited

U.S. PATENT DOCUMENTS

| | | | |
|---|---|---|---|
| 3,661,917 | 5/1972 | Kaiser et al. | 514/320 |
| 3,743,737 | 7/1973 | Kaiser et al. | 514/320 |
| 4,661,596 | 4/1987 | Kreft | 546/172 |
| 4,876,346 | 10/1989 | Musser et al. | 514/312 |
| 4,918,081 | 4/1990 | Huang et al. | 514/314 |
| 4,920,130 | 4/1990 | Huang et al. | 514/314 |
| 4,920,131 | 4/1990 | Huang et al. | 514/314 |
| 4,920,132 | 4/1990 | Huang et al. | 514/314 |
| 4,920,133 | 4/1990 | Huang et al. | 514/314 |
| 5,006,534 | 4/1991 | Mohrs | 514/311 |

FOREIGN PATENT DOCUMENTS

| | | |
|---|---|---|
| 0110405 | 11/1983 | European Pat. Off. |
| 0181568 | 10/1985 | European Pat. Off. |
| 0190722 | 8/1986 | European Pat. Off. |
| 0271287 | 6/1988 | European Pat. Off. |
| 0200101 | 12/1988 | European Pat. Off. |
| 0349062 | 6/1989 | European Pat. Off. ......... 514/311 |

OTHER PUBLICATIONS

J. Med. Chem 30:96–104 (1987).

*Primary Examiner*—Robert T. Bond
*Assistant Examiner*—E. C. Ward
*Attorney, Agent, or Firm*—Cushman, Darby & Cushman

[57] ABSTRACT

The invention concerns a heterocyclic cycloalkane of the formula I $$Q-A-X-Ar-\underset{R^3}{\overset{OR^1}{\underset{|}{C}}}-R^2 \qquad I$$

wherein Q is an optionally substituted 6-membered monocyclic or 10-membered bicyclic heterocyclic moiety containing one or two nitrogen atoms;
A is (1–6C)alkylene, (3–6C)alkenylene, (3–6C)alkynylene or cyclo(3–6C)alkylene;
X is oxy, thio, sulphinyl, sulphonyl or imino;
Ar is phenylene which may optionally bear one or two substituents or Ar is an optionally substituted 6-membered heterocyclene moiety containing up to three nitrogen atoms;
$R^1$ is hydrogen, (1–6C)alkyl, (3–6C)alkenyl, (3–6C)alkynyl, cyano-(1–4C)alkyl or (2–4C)alkanoyl, or optionally substituted benzoyl; and $R^2$ and $R^3$ together form a (3–6C)alkylene group which, together with the carbon atom to which $R^2$ and $R^3$ are attached, defines a ring having 4 to 7 ring atoms, and which ring may bear one or two substituents;
or a pharmaceutically-acceptable salt thereof.

The compounds of the invention are inhibitors of the enzyme 5-lipoxygenase.

9 Claims, No Drawings

HETEROCYCLIC CYCLOALKANES

This is a continuation of application Ser. No. 07/485,492, filed on Feb. 27, 1990, which was abandoned.

This invention concerns novel heterocyclic cycloalkanes and more particularly novel heterocyclic cycloalkanes which are inhibitors of the enzyme 5-lipoxygenase (hereinafter referred to as 5- LO). The invention also concerns processes for the manufacture of said heterocyclic cycloalkanes and novel pharmaceutical compositions containing said heterocyclic cycloalkanes. Also included in the invention is the use of said heterocyclic cycloalkanes in the treatment of various inflammatory and/or allergic diseases in which the direct or indirect products of 5-LO catalysed oxidation of arachidonic acid are involved, and the production of new medicaments for such use.

As stated above the heterocyclic cycloalkanes described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various inflammatory and allergic diseases such as arthritic diseases, asthma, allergic rhinitis, atopic dermatitis, psoriasis, cardiovascular and cerebrovascular disorders and inflammatory bowel disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

We have now discovered that certain heterocyclic cycloalkanes are effective as inhibitors of the enzyme 5-LO and thus of leukotriene biosyntheses. Thus, such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided a heterocyclic cycloalkane of the formula I (set out hereinafter) wherein Q is a 6-membered monocyclic or 10-membered bicyclic heterocyclic moiety containing one or two nitrogen atoms which may optionally bear one, two or three substituents selected from halogeno, hydroxy, oxo, carboxy, cyano, amino, (1–4C)alkyl, (1–4C)alkoxy, fluoro-(1–4C)alkyl, (1–4C)alkylamino, di-[(1–4C)alkyl]amino, hydroxy-(1–4C)alkyl, amino-(1–4C)alkyl, (1–4C)alkylamino-(1–4C)alkyl, di-[(1–4C)alkyl]amino-(1–4C)alkyl, amino-(2–4C)alkoxy, (1–4C)alkylamino-(2–4C)alkoxy, di-[(1–4C)alkyl]amino-(2–4C)alkoxy and phenyl-(1–4C)alkyl; wherein A is (1–6C)alkylene, (3–6C)alkenylene, (3–6C)alkynylene or cyclo(3–6C)alkylene; where X is oxy, thio, sulphinyl, sulphonyl or imino; wherein Ar is phenylene which may optionally bear one or two substituents selected from halogeno, hydroxy, amino, nitro, cyano, ureido, carbamoyl, (1–4C)alkyl, (3–4C)alkenyloxy, (1–4C)alkoxy, (1–4C)alkylthio, (1–4C)alkylsulphinyl, (1–4C)alkylsulphonyl, (1–4C)alkylamino, di-[(1–4C)alkyl]amino, fluoro-(1–4C)alkyl, (1–4C)alkoxycarbonyl, N-[(1–4C)alkyl]carbamoyl, N,N-di-[(1–4C)alkyl]carbamoyl, (2–4C)alkanoylamino, cyano-(1–4C)alkoxy, carbamoyl-(1–4C)alkoxy, amino-(2–4C)alkoxy, (1–4C)alkylamino-(2–4C)alkoxy, di-[(1–4C)alkyl]amino-(2–4C)alkoxy and (1–4C)alkoxycarbonyl-(1–4C)alkoxy; or Ar is a 6-membered heterocyclene moiety containing up to three nitrogen atoms which may optionally bear one or two substituents selected from halogeno, hydroxy, amino, cyano, (1–4C)alkyl, (1–4C)alkoxy, (1–4C)alkylamino and di-[(1–4C)alkyl]amino; wherein $R^1$ is hydrogen, (1–6C)alkyl, (3–6C)alkenyl, (3–6C)alkynyl, cyano-(1–4C)alkyl or (2–4C)alkanoyl, or $R^1$ is benzoyl which may optionally bear a substituent selected from halogeno, (1–4C)alkyl and (1–4C)alkoxy; and wherein $R^2$ and $R^3$ together form a (3–6C)alkylene group which, together with the carbon atom to which $R^2$ and $R^3$ are attached, defines a ring having 4 to 7 ring atoms, and which ring may bear one or two substituents, which may be the same or different, selected from hydroxy, (1–4C)alkyl, (1–4C)alkoxy, (1–4C)alkylthio, (1–4C)alkylsulphinyl and (1–4C)alkylsulphonyl, or which ring may bear a (1–4C)alkylenedioxy substituent; or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of formula I defined above may exist in optically active or racemic forms by virtue of one or more substituents containing an asymmetric carbon atoms, the invention includes in its definition of active ingredient any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

It is also be understood that, insofar as certain of the compounds of the formula I as defined above may exhibit the phenomenon of tautomerism, for example a compound of the formula I wherein Q bears an oxo or hydroxy substituent, and as any formula drawings presented herein may represent only one of the possible tautomeric forms the invention includes in its definition any tautomeric form of a compound of the formula I which possesses the property of inhibiting 5-LO and is not to be limited merely to any one tautomeric form utilised within the formulae drawings.

Suitable values for the generic terms referred to above include those set out below.

A suitable value for Q when it is a 6-membered monocyclic or 10-membered bicyclic heterocyclic moiety containing one or two nitrogen atoms is, for example, pyridyl, pyridazinyl, pyrimidinyl, pyrazinyl, quinolyl, isoquinolyl, cinnolinyl, quinazolinyl, quinoxalinyl, phthalazinyl or naphthyridinyl, or a hydrogenated derivative thereof such as, for example, 1,2-dihydropyridyl or 1,2-dihydroquinolyl. The heterocyclic moiety may be attached through any available nitrogen atom and it may bear a substituent on any available position including on any available nitrogen atom.

When Q is a 10-membered bicyclic heterocyclic moiety containing one or two nitrogen atoms it will be appreciated that Q may be attached to A from either of the two rings of the bicyclic heterocyclic moiety.

Conveniently Q is, for example, 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 2-quinolyl, 3-quinolyl, 5-quinolyl, 6-quinolyl, 7-quinolyl, 1-isoquinolyl, 3-isoquinolyl, 6-isoquinolyl, 7-isoquinolyl, 3-cinnolyl, 6-cinnolyl, 7-cinnolyl, 2-quinazolinyl, 4-quinazolinyl, 6-quinazolinyl, 7-quinazolinyl, 2-quinoxalinyl, 5-quinoxalinyl, 6-quinoxalinyl, 1-phthalazinyl, 6-phthalazinyl, 1,5-naphthyridin-2-yl, 1,5-naphthyridin-3-yl, 1,6-naphthyridin-3-yl, 1,6-naphthyridin-7-yl, 1,7-naphthyridin-3-yl, 1,7-naphthyridin-6-yl, 1,8-naphthyridin-3-yl, 2,6-naphthyridin-3-yl or 2,7-naphthyridin-3-yl.

A suitable value for a halogeno substituent which may be present on Q, Ar or $R^1$ is, for example, fluoro, chloro, bromo or iodo.

A suitable value for a (1–4C)alkyl substituent which may be present on Q, Ar or $R^1$ is, for example, methyl, ethyl, propyl, isopropyl, butyl, isobutyl or sec-butyl.

A suitable value for a (1–4C)alkoxy substituent which may be present on Q, Ar or $R^1$ is, for example, methoxy, ethoxy, propoxy, isopropoxy or butoxy.

A suitable value for a fluoro-(1–4C)alkyl substituent which may be present on Q or Ar, is, for example, fluoromethyl, difluoromethyl, trifluoromethyl, 2-fluoroethyl, 2,2,2-trifluoroethyl or pentafluoroethyl.

A suitable value for A when it is (1–6C)alkylene is, for example, methylene, ethylene, ethylidene, trimethylene, propylidene, tetramethylene or pentamethylene; when it is (3–6C)alkenylene is, for example, 1-propenylene, 2-methylprop-1-enylene, 3-methylprop-1-enylene, 1-butenylene or 2-butenylene; and when it is (3–6C)alkynylene is, for example, 1-propynylene, 3-methylprop-1-ynylene, 1-butynylene or 2-butynylene.

A suitable value for A when it is cyclo(3–6C)alkylene is, for example, cyclopropylidene, 1,2-cyclopropylene, cyclopentylidene, 1,2-cyclopentylene, cyclohexylidene or 1,4-cyclohexylene.

A suitable value for Ar when it is phenylene is, for example, 1,3-phenylene or 1,4-phenylene.

A suitable value for Ar when it is a 6-membered heterocyclene moiety containing up to three nitrogen atoms is, for example, pyridylene, pyrimidinylene, pyridazinylene, pyrazinylene or 1,3,5-triazinylene. Conveniently Ar when it is a 6-membered heterocyclene moiety containing up to three nitrogen atoms is, for example, 2,4-, 2,5-, 3,5- or 2,6-pyridylene, 2,4-, 2,5- or 4,6-pyridimidinylene, 3,5-, or 3,6-pyridazinylene or 2,5- or 2,6-pyrazinylene.

Suitable values for substituents which may be present on Q or Ar include, for example:

| | |
|---|---|
| for (1–4C)alkylamino: | methylamino, ethylamino propylamino and butylamino; |
| for di-[(1–4C)alkyl]amino: | dimethylamino, diethylamino and dipropylamino; |
| for amino-(2–4C)alkoxy: | 2-aminoethoxy, 3-aminopropoxy and 4-aminobutoxy; |
| for (1–4C)alkylamino-(2–4C)alkoxy: | 2-methylaminoethoxy, 3-methylaminopropoxy and 2-ethylaminoethoxy; |
| for di-[(1–4C)alkyl]amino-(2–4C)alkoxy: | 2-dimethylaminoethoxy-3-dimethylaminopropoxy and 2-diethylaminoethoxy. |

Suitable values for substituents which may be present on Q include, for example:

| | |
|---|---|
| for hydroxy-(1–4C)alkyl: | hydroxymethyl, 1-hydroxyethyl, 2-hydroxyethyl, 2-hydroxypropyl and 3-hydroxypropyl; |
| for amino-(1–4C)alkyl: | aminomethyl, 1-aminoethyl, 2-aminoethyl, 2-aminopropyl and 3-aminopropyl; |
| for (1–4C)alkylamino-(1–4C)alkyl: | methylaminomethyl, 2-methylaminoethyl, 3-methylaminopropyl, ethylaminomethyl and 2-ethylaminoethyl; |
| for di-[(1–4C)alkyl]amino-(1–4C)alkyl: | dimethylaminomethyl, 2-dimethylaminoethyl, 3-dimethylaminopropyl, diethylaminomethyl and 2-diethylaminoethyl; |
| for phenyl-(1–4C)alkyl: | benzyl, phenethyl and 3-phenylpropyl. |

Suitable values for substituents which may be present on Ar include, for example:

| | |
|---|---|
| for (3–4C)alkenyloxy: | allyloxy, methylallyloxy, but-2-enyloxy and but-3-enyloxy; |
| for (1–4C)alkylthio: | methylthio, ethylthio, propylthio, isopropylthio and butylthio; |
| for (1–4C)alkylsulphinyl: | methylsulphinyl, ethylsulphinyl, propylsulphinyl, isopropylsulphinyl and butylsulphinyl; |
| for (1–4C)alkylsulphonyl: | methylsulphonyl, ethylsulphonyl, propylsulphonyl, isopropylsulphonyl and butylsulphonyl; |
| for (1–4C)alkoxycarbonyl: | methoxycarbonyl, ethoxycarbonyl and tert-butyoxycarbonyl; |
| for N-[(1–4C)alkyl]-carbamoyl: | N-methylcarbamoyl, N-ethylcarbamoyl and N-propylcarbamoyl; |
| for N,N-di-[1–4C)alkyl]-carbamoyl: | N,N-dimethylcarbamoyl and N,N-diethylcarbamoyl; |
| for (2–4C)alkanoylamino: | acetamido, propionamido and butyramido; |
| for cyano-(1–4C)alkoxy: | cyanomethoxy, 2-cyanoethoxy and 3-cyanopropoxy; |
| for carbamoyl-(1–4C)alkoxy: | carbamoylmethoxy, 2-carbamoylethoxy and 3-carbamoylpropoxy; |
| for (1–4C)alkoxycarbonyl-(1–4C)-alkoxy: | methoxycarbonylmethoxy, 2-methoxycarbonylethoxy, ethoxycarbonylmethoxy and 2-ethoxycarbonylethoxy. |

A suitable value for $R^1$ when it is (1–6C)alkyl is, for example, methyl, ethyl, propyl, butyl, pentyl or hexyl.

A suitable value for $R^1$ when it is (3–6C)alkenyl is, for example, allyl, 2-butenyl or 3-butenyl; and when it is (3–6C)alkynyl is, for example, 2-propynyl or 2-butynyl.

A suitable value for $R^1$ when it is (2–4C)alkanoyl is, for example, acetyl, propionyl or butyryl.

A suitable value for $R^1$ when it is cyano-(1–4C)alkyl is, for example, cyanomethyl, 2-cyanoethyl or 3-cyanopropyl.

A suitable value for $R^2$ and $R^3$ when they together form a (3–6C)alkylene group which, together with the carbon atom to which $R^2$ and $R^3$ are attached, defines a ring having 4 to 7 ring atoms is, for example, trimethylene, tetramethylene, pentamethylene or hexamethylene. Suitable values for the one or two substituents which may be present on said 4- to 7-membered ring include for example:

| | |
|---|---|
| for (1–4C)alkyl: | methyl, ethyl, propyl, isopropyl and butyl; |
| for (1–4C)alkoxy: | methoxy, ethoxy, propoxy, isopropoxy and butoxy; |
| for (1–4C)alkythio: | methylthio, ethylthio, propylthio, isopropylthio and butylthio; |
| for (1–4C)alkylsulphinyl: | methylsulphinyl, ethylsulphinyl, propylsulphinyl, isopropylsulphinyl and butylsulphinyl; |
| for (1–4C)alkylsulphonyl: | methylsulphonyl, ethylsulphonyl, propylsulphonyl, isopropylsulphonyl and butylsulphonyl; |
| for (1–4C)alkylenedioxy: | methylenedioxy and ethylenedioxy. |

A suitable pharmaceutically-acceptable salt of a heterocyclic cycloalkane of the invention which is sufficiently basic is an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a heterocyclic cycloalkane of the invention which is sufficiently acidic (for example a heterocyclic cycloalkane of the invention which contains a carboxy group) is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention are, for example, heterocyclic cycloalkanes of the formula I wherein:

(a) Q is 2-pyridyl, 3-pyridyl, 3-pyridazinyl, 2-pyrimidinyl or 2-pyrazinyl which may optionally bear one substituent selected from chloro, hydroxy, cyano, methyl, methoxy and trifluoromethyl; and A, X, Ar, $R^1$, $R^2$ and $R^3$ have any of the meanings defined hereinbefore;

(b) Q is 2-pyridyl or 3-pyridyl; A is 1-propenylene or 1-propynylene; and X is oxy; and Ar, $R^1$, $R^2$ and $R^3$ have any of the meanings defined hereinbefore;

(c) Q is 2-quinolyl, 3-quinolyl, 6-quinolyl, 7-quinolyl, 3-isoquinolyl, 6-isoquinolyl, 7-isoquinolyl, 3-cinnolyl, 2-quinazolinyl, 6-quinazolinyl, 2-quinoxalinyl, 6-quinoxalinyl, 6-phthalazinyl, 1,7-naphthyridin-3-yl, 1,7-naphthyridin-6-yl, 1,8-naphthyridine-3-yl or 2,7-naphthyridin-3-yl which may optionally bear one or two substituents selected from fluoro, chloro, hydroxy, oxo, cyano, methyl, methoxy and trifluoromethyl; and A, X, Ar, $R^1$, $R^2$ and $R^3$ have any of the meanings defined hereinbefore;

(d) Q is 3-quinolyl, 5-quinolyl, 6-quinolyl, 7-quinolyl, 3-isoquinolyl, 2-quinazolinyl, 6-quinazolinyl or 6-quinoxalinyl which may optionally bear one, two or three substituents selected from fluoro, chloro, hydroxy, oxo, methyl, ethyl, propyl, trifluoromethyl, 2-fluoroethyl, 2-dimethylaminoethyl and benzyl; and A, X, Ar, $R^1$, $R^2$ and $R^3$ have any of the meanings defined hereinbefore;

(e) Q is 1,2-dihydro-2-oxoquinolin-3-yl, 1,2-dihydro-2-oxoquinolin-6-yl, 1,2-dihydro-2-oxoquinolin-7-yl, 3,4-dihydro-4-oxoquinazolin-6-yl, 1,2-dihydro-2-oxo-1,7-naphthyridin-3-yl or 1,2-dihydro-2-oxo-1,8-naphthyridine-3-yl which may optionally bear one or two substituents selected from fluoro, chloro, cyano, methyl, methoxy and trifluoromethyl; and A, X, Ar, $R^1$, $R^2$ and $R^3$ have any of the meanings defined hereinbefore;

(f) Q is 1,2-dihydro-2-oxoquinolin-3-yl, 1,2-dihydro-2-oxoquinolin-5-yl, 1,2-dihydro-2-oxoquinolin-6-yl or 1,2-dihydro-2-oxoquinoline-7-yl which may optionally bear one or two substituents selected from fluoro, chloro, methyl, ethyl, propyl, trifluoromethyl, 2-fluoroethyl, 2-dimethylaminomethyl and benzyl; and A, X, Ar, $R^1$, $R^2$ and $R^3$ have any of the meanings defined hereinbefore;

(g) Q is 1,2-dihydro-2-oxoquinoline-3-yl, 1,2-dihydro-2-oxoquinoline-5-yl, 1,2-dihydro-2-oxoquinolin-6-yl or 1,2-dihydro-2-oxoquinolin-7-yl which bears a 1-substituent selected from methyl, ethyl, propyl, 2-fluoroethyl, 2-dimethylaminoethyl and benzyl, and which may optionally bear a substituent selected from fluoro, chloro and trifluoromethyl; and A, X, Ar, $R^1$, $R^2$ and $R^3$ have any of the meanings defined hereinbefore;

(h) A is methylene, ethylene, trimethylene, 1-propenylene, 2-methylprop-1-enylene or 1-propynylene and Q, X, Ar, $R^1$, $R^2$ and $R^3$ have any of the meanings defined hereinbefore;

(i) A is methylene, 1-propenylene or 1-propynylene; and Q, X, Ar, $R^1$, $R^2$ and $R^3$ have any of the meanings defined hereinbefore;

(j) X is oxy and Q, A, Ar, $R^1$, $R^2$ and $R^3$ have any of the meanings defined hereinbefore;

(k) Ar is 1,3-phenylene or 1,4-phenylene which may optionally bear one substituent selected from fluoro, chloro, hydroxy, amino, nitro, methyl, methoxy, methylthio, methylsulphinyl, methylsulphonyl, methylamino, dimethylamino, trifluoromethyl, acetamido, cyanomethoxy and carbamoylmethoxy; and Q, S, X, $R^1$, $R^2$ and $R^3$ have any of the meanings defined hereinbefore;

(l) Ar is 1,3-phenylene or 1,4-phenylene which may optionally bear one or two substituents selected from fluoro, chloro, hydroxy, amino, ureido, methoxy and trifluoromethyl and X, A, X, $R^2$, $R^2$ and $R^3$ have any of the meanings defined hereinbefore;

(m) Ar is 2,4-, 2,5-, 3,5- or 2,6-pyridylene or 4,6-pyrimidinylene which may optionally bear on substituent selected from chloro, methyl and methoxy; and Q, A, X, $R^1$, $R^2$ and $R^3$ have any of the meanings defined hereinbefore;

(n) Ar is 3,5-pyridylene; and Q, A, X, $R^1$, $R^2$ and $R^3$ have any of the meanings defined hereinbefore;

(o) $R^1$ is hydrogen, methyl, ethyl, allyl, 2-propynyl or cyanomethyl; and Q, A, X, Ar, $R^2$ and $R^3$ have any of the meanings defined hereinbefore;

(p) $R^1$ is methyl, ethyl, allyl or 2-propynyl; and Q, A, X, Ar, $R^2$ and $R^3$ have any of the meanings defined hereinbefore;

(q) $R^2$ and $R^3$ together form a tetramethylene or pentamethylene group which, together with the carbon atom to which $R^2$ and $R^3$ are attached, defines a ring having 5 or 6 ring atoms and which ring may bear a substituent selected from hydroxy, methyl, methoxy, ethoxy, methylthio, methylsulphinyl, methylsulphonyl and methylenedioxy; and Q, A, X, Ar and $R^1$ have any of the meanings defined hereinbefore; or (r) $R^2$ and $R^3$ together form a tetramethylene group which, together with the carbon atom to which $R^2$ and $R^3$ are attached, defines a ring having 5 ring atoms and which ring may bear a substituent selected from hydroxy and methoxy; and Q, A, X, Ar and $R^1$ have any of the meanings defined hereinbefore;
or a pharmaceutically-acceptable salt thereof.

A particular compound of the invention comprises a heterocyclic cycloalkane of the formula I wherein Q is pyridyl, pyrimidinyl, pyrazinyl, quinolyl, isoquinolyl, quinazolinyl or quinoxalinyl which may optionally bear one, two or three substituents selected from fluoro, chloro, hydroxy, oxo, methyl, ethyl, propyl, trifluoromethyl, 2-fluoromethyl, 2-dimethylaminoethyl and benzyl; wherein A is methylene, 1-propenylene or 1-propynylene; wherein X is oxy; wherein A is 1,3-phenylene or 1,4-phenylene which may optionally bear one or two substituents selected from fluoro, chloro, hydroxy, amino, ureido, methoxy and trifluoromethyl or Ar is 3,5-pyridylene; wherein $R^1$ is methyl, ethyl, allyl or 2-propynyl; and wherein $R^2$ and $R^3$ together form a tetramethylene or pentamethylene group which, together with the carbon atom to which $R^2$ and $R^3$ are attached, defines a ring having 5 or 6 ring atoms and which ring may bear a substituent selected from hydroxy, methyl, methoxy and ethoxy; or a pharmaceutically-acceptable salt thereof.

A further particular compound of the invention comprises a heterocyclic cycloalkane of the formula I wherein Q is 2-pyridyl, 3-pyridyl, 3-pyridazinyl, 2-pyrimidinyl or 2-pyrazinyl which may optionally bear one substituent selected from chloro, hydroxy, cyano, methyl, methoxy and trifluoromethyl, or Q is 2-quinolyl, 3-quinolyl, 6-quinolyl, 7-quinolyl, 3-isoquinolyl, 6-isoquinolyl, 7-isoquinolyl, 3-cinnolyl, 2-quinazolinyl, 6-quinazolinyl, 2-quinoxalinyl, 6-quinoxalinyl, 6-phthalazinyl, 1,7-naphthyridin-3-yl, 1,7-naphthyridin-6-yl, 1,8-naphthyridin-3-yl or 2,7-naphthyridine-3-yl which may optionally bear one or two substituents selected from fluoro, chloro, hydroxy, oxo, cyano, methyl, methoxy and trifluoromethyl; A is methylene, ethylene, trimethylene, 1-propylene, 2-methylprop-1-enylene or 1-propynylene; X is oxy; Ar is 1,3-phenylene or 1,4-phenylene which may optionally bear one substituent selected from fluoro, chloro, hydroxy, amino, nitro, methyl, methoxy, methylthio, methylsulphinyl, methylsulphonyl, methylamino, dimethylamino, trifluoromethyl, acetamido, cyanomethoxy and carbamoylmethoxy, or Ar is 2,4-, 2,5-, 3,5- or 2,6-pyridylene or 4,6-pyrimidinylene which may optionally bear one substituent selected from chloro, methyl and methoxy; $R^1$ is methyl, ethyl, allyl or 2-propynyl; and $R^2$ and $R^3$ together form a tetramethylene or pentamethylene group which, together with the carbon atom to which $R^2$ and $R^3$ are attached, defines a ring having 5 or 6 ring atoms and which ring may bear a substituent selected from hydroxy, methyl, methoxy, ethoxy, methylthio, methylsulphinyl, methylsulphonyl and methylenedioxy; or a pharmaceutically-acceptable salt thereof.

A further particular compound of the invention comprises a heterocyclic cycloalkane of the formula I wherein Q is 2-pyridyl, 3-pyridyl, 3-quinolyl, 5-quinolyl, 6-quinolyl, 7-quinolyl or 6-quinoxalinyl which may optionally bear one or two substituents selected from hydroxy, oxo, methyl, ethyl, propyl, 2-fluoroethyl, 2-dimethylaminoethyl and benzyl; wherein A is methylene, 1-propenylene or 1-propynylene; wherein X is oxy; wherein Ar is 1,3-phenylene or 1,4-phenylene which may optionally bear one to two substituents selected from fluoro, chloro, amino, methoxy and trifluoromethyl, or Ar is 3,5-pyridylene; wherein $R^1$ is methyl, ethyl or allyl; and wherein $R^2$ and $R^3$ together form a tetramethylene group which, together with the carbon atom to which $R^2$ and $R^3$ are attached, defines a ring having 5 ring atoms and which ring may bear a substituent selected from hydroxy and methoxy; or a pharmaceutically-acceptable salt thereof.

A preferred compound of the invention comprises a heterocyclic cycloalkane of the formula I wherein Q is 1,2-dihydro-2-oxoquinolin-3-yl, 1,2-dihydro-2-oxoquinolin-5-yl, 1,2-dihydro-2-oxoquinolin-6-yl or 1,2-dihydro-2-oxoquinolin-7-yl which bears a 1-substituent selected from methyl, ethyl and 2-fluoroethyl; wherein A is methylene; wherein X is oxy; wherein Ar is 1,3-phenylene which may optionally bear one fluoro substituent; wherein $R^1$ is methyl; and wherein $R^2$ and $R^3$ together form a tetramethylene group which, together with the carbon atom to which $R^2$ and $R^3$ are attached, defines a ring having 5 ring atoms and which ring bears a methoxy substituent; or a pharmaceutically-acceptable salt thereof.

An especially preferred compound of the invention comprises a heterocyclic cycloalkane of the formula I wherein Q is 2-pyridyl, 1,2-dihydro-1-methyl-2-oxoquinolin-3-yl or 6-quinoxalinyl; A is methylene or 1-propynylene; X=oxy; Ar is 1,3-phenylene or 5-fluoro-1,3-phenylene; $R^1$ is methyl; and $R^2$ and $R^3$ together form a tetramethylene group, which, together with the carbon atom to which $R^2$ and $R^3$ are attached, defines a ring having 5 ring atoms and which ring bears a 2-methoxy substituent; or a pharmaceutically-acceptable salt thereof.

Specific especially preferred compounds of the invention include, for example, the following heterocyclic cycloalkanes of the formula I, or pharmaceutically-acceptable salts thereof:
trans-1,2-dimethoxy-1-[3-(3-(2-pyridyl)prop-2-yn-1-yloxy)phenyl]cyclopentane,
(1RS,2SR)-1-[5-fluoro-3-(quinoxalin-6-ylmethoxy)-phenyl]-1,2-dimethoxycyclopentane and
(1RS,2SR)-1-[5-fluoro-3-(1,2-dihydro-1-methyl-2-oxoquinolin-6-ylmethoxy)phenyl]-1,2-dimethoxycyclopentane.

A compound of the invention comprising a heterocyclic cycloalkane of the formula I, or a pharmaceutically-acceptable salt thereof, may be prepared by any process known to be applicable to the preparation of structurally-related compounds. Such procedures are provided as a further feature of the invention and are illustrated by the following representative examples in which, unless otherwise stated, Q, A, X, Ar, $R^1$, $R^2$ and $R^3$ have any of the meanings defined hereinbefore.

(a) The alkylation, in the presence of a suitable reagent, of a compound of the formula II with a compound of the formula Q-A-Z wherein Z is a displaceable group; provided that, when there is an amino, alkylamino, hydroxy or carboxy group in Q, Ar, $R^1$, $R^2$ or $R^3$, any amino, alkylamino or carboxy group is protected by a conventional protecting group and any hydroxy group may be protected by a conventional protecting group or alternatively any hydroxy group need not be protected; whereafter any undesired protecting group in Q, Ar, $R^1$, $R^2$ or $R^3$ is removed by conventional means.

A suitable displaceable group Z is, for example, a halogeno, sulphonyloxy or hydroxy group, for example a chloro, bromo, iodo, methanesulphonyloxy or toluene-p-sulphonyloxy group.

A suitable reagent for the alkylation reaction when Z is a halogeno or sulphonyloxy group is, for example, a suitable base, for example, an alkali or alkaline earth metal carbonate, hydroxide or hydride, for example sodium carbonate, potassium carbonate, sodium hydroxide, potassium hydroxide, sodium hydride or potassium hydride. The alkylation reaction is preferably performed in a suitable inert solvent or diluent, for example N,N-dimethylformamide, N,N-dimethylacetamide, dimethylsulphoxide, acetone, 1,2-dimethoxyethane or tetrahydrofuran, and at a temperature in the range, for example, $-10°$ to $150°$ C., conveniently at or near ambient temperature.

A suitable reagent for the alkylation reaction when Z is a hydroxy group is, for example, the reagent obtained when a compound of the formula Q—A—OH is reacted with a di-(1-4C)alkyl azodicarboxylate in the presence of a triarylphosphine, for example with diethyl azodicarboxylate in the presence of triphenylphosphine. The alkylation reaction is preferably performed in a suitable inert solvent or diluent, for example acetone, 1,2-dimethoxyethane or tetrahydrofuran, and at a temperature in the range, for example, $10°$ to $80°$ C., conveniently at or near ambient temperature.

A suitable protecting group for an amino or alkylamino group is, for example, an acyl group for example a (1-4C)alkanoyl group (especially acetyl), a (1-4C)alkoxycarbonyl group (especially methoxycarbonyl, ethoxycarbonyl or t-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl, alkoxycarbonyl or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-charcoal.

A suitable protecting group for a carboxy group is, for example, an esterifying group, for example a (1-4-C)alkyl group (especially methyl or ethyl) or an arylmethyl group (especially benzyl). The deprotection conditions for the above protecting groups necessarily vary with the choice of protecting group. Thus, for example, an esterifying group such as an alkyl or arylmethyl group may be removed, for example, by hydrolysis with a suitable base such as an alkali metal hydroxide, for example lithium or sodium hydroxide. Alternatively an esterifying group such as an arylmethyl group may be removed, for example, by hydrogenation over a catalyst such as palladium-on-charcoal.

A suitable protecting group for a hydroxy group is, for example, an acyl group, for example a (1-4C)alkanoyl group (especially acetyl), an aroyl group (especially benzoyl) or a arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

The starting materials of the formula II may be obtained by standard procedures of organic chemistry. The preparation of examples of such starting materials is described within the accompanying non-limiting Examples which are provided for the purpose of illustration only. Other necessary starting materials are obtainable by analogous procedures to those described or by modification thereto which are within the ordinary skill of an organic chemist. Thus the starting material of the formula II may be obtained, for example, by deprotecting a protected heterocyclic cycloalkane of the formula III wherein $R^4$ is a protecting group and X, Ar, $R^1$, $R^2$ and $R^3$ have the meanings defined hereinbefore.

A suitable protecting group $R^4$ is, for example, an arylmethyl group (especially benzyl), a tri-(1-4C)alkylsilyl group (especially trimethylsilyl or t-butyldimethylsilyl), an aryldi-(1-4C)alkylsilyl group (especially dimethylphenylsilyl), a (1-4C)alkyl group (especially methyl), a (1-4C)alkoxymethyl group (especially methoxymethyl) or a tetrahydropyranyl group (especially tetrahydropyran-2-yl). The deprotection conditions for the above protecting groups will necessarily vary with the choice of protecting groups. Thus, for example, an arylmethyl group such as a benzyl group may be removed, for example, by hydrogenation over a catalyst such as palladium-on-charcoal. Alternatively a trialkylsilyl or an aryldialkylsilyl group such as a t-butyldimethylsilyl or a dimethylphenylsilyl group may be removed, for example, by treatment with a suitable acid such as hydrochloric, sulphuric, phosphoric or trifluoroacetic acid or with an alkali metal or ammonium fluoride such as sodium fluoride or, preferably, tetrabutylammonium fluoride. Alternatively an alkyl group may be removed, for example, by treatment with an alkali metal (1-4C)alkylsulphide such as sodium thioethoxide or, for example, by treatment with an alkali metal diarylphosphide such as lithium diphenylphosphide or, for example, by treatment with a boron or aluminium trihalide such as boron tribromide. Alternatively a (1-4C)alkoxymethyl group or tetrahydropyranyl group may be removed, for example, by treatment with a suitable acid such as hydrochloric or trifluoroacetic acid.

The protecting group $R^4$ may be, for example, a tri-(1-4C)alkylsilyl group which can be removed while the protecting group for any amino, alkylamino, carboxy or hydroxy group in Ar, $R^1$, $R^2$ or $R^3$ is retained.

The protected starting material of the formula III may be obtained by standard procedures of organic chemistry as illustrated in the accompanying non-limiting Examples. Thus, for example, the protected starting material of the formula III, wherein $R^4$ has the meaning defined hereinbefore, may be obtained by the alkylation of the tertiary alcohol of the formula IV with an alkylating agent of the formula $R^1$—Z, wherein Z is a displaceable group as defined hereinbefore other than hydroxy, in the presence of a suitable base as defined hereinbefore, and provided that any amino, alkylamino or hydroxy group in Ar, $R^2$ or $R^3$ is protected by a conventional protecting group.

The tertiary alcohol starting material of the formula IV may be obtained by the reaction of a compound of the formula $R^4{}^{13}X$—Ar—Z, wherein $R^4$ and Ar have the meanings defined hereinbefore and Z is a halogeno group as defined hereinbefore and provided that any amino, alkylamino or hydroxy group in Ar is protected with a conventional protecting group, with either an organometallic compound of the formula $R^5$—M, wherein $R^5$ is a (1-6C)alkyl group such as butyl and M is a metallic group, for example lithium, to give an organometallic compound of the formula $R^4$—X—Ar—M, or with a metal such as magnesium to give an organometallic compound of the formula $R^4$—X—Ar—M—Z; whereafter either of these organometallic compounds may be reacted with a ketone of the formula $R^2$—CO—$R^3$, wherein $R^2$ and $R^3$ have the meanings defined hereinbefore, and provided that any hydroxy group in $R^2$ and $R^3$ is protected by a conventional protecting group.

(b) The alkylation, in the presence of a suitable base as defined hereinbefore, of a compound of the formula V with a compound of the formula $R^1$—Z, wherein $R^1$ and Z have the meanings defined hereinbefore, provided that, when there is an amino, imino, alkylamino, hydroxy or carboxy group in Q, X, Ar, $R^2$ or $R^3$, any amino, imino, alkylamino, hydroxy or carboxy group is protected by a conventional protecting group; whereafter any undesired protecting group in Q, X, Ar, $R^2$ or $R^3$ is removed by conventional means.

The starting materials of formula V may be obtained by standard procedures of organic chemistry. The preparation of examples of such starting materials is described within the accompanying non-limiting Examples which are provided for the purpose of illustration only. Other necessary starting materials are obtainable by analogous procedures to those described or by modification thereto which are within the ordinary skill of an organic chemist. Thus the tertiary alcohol starting material of the formula V may be obtained, for example, by the alkylation, in the presence of a suitable base, of a compound of the formula HX—Ar—Z, wherein Ar has the meaning defined hereinbefore and Z is a halogeno group as defined hereinbefore, with a compound of the formula Q—A—Z, wherein Q, A and Z have the meanings defined hereinbefore, and provided that any amino, alkylamino, carboxy or hydroxy group in Q or Ar is protected by a conventional protecting group, to give a compound of the formula Q—A—X—Ar—Z. Alternatively the compound of the formula Q—A—Z—Ar—Z may be obtained, for example, by the alkylation, in the presence of a suitable base, of a compound of the formula Q—A—XH, wherein Q, A and X have the meanings defined hereinbefore, with a compound of the formula Z—Ar—Z, wherein Z and Ar have the meanings defined hereinbefore. The product so obtained may be treated either with an organometallic compound of the formula $R^5$—M, wherein $R^5$ is a (1-6C)alkyl group such as butyl and M is a metallic group, for example lithium, to give an organometallic compound of the formula Q—A—X—Ar—M, or with a metal such as magnesium to give an organometallic compound of the formula Q—A—X—Ar—M—Z. Either of these organometallic compounds may be reacted with a ketone of the formula $R^2$—CO—$R^3$, provided that any imino or hydroxy group in X, $R^2$ or $R^3$ is protected by a conventional protecting group, to give the required tertiary alcohol starting material of the formula V.

(c) For the production of those compounds of the formula I wherein A is a (3-6C)alkynylene group, the coupling, in the presence of a suitable organometallic catalyst, of a heterocyclic compound of the formula Q—Z, wherein Q has the meaning defined hereinbefore and Z is a halogeno group such as iodo, with an ethynyl compound of the formula VI, wherein $A^1$ is (1-4C)alkylene and X, Ar, $R^1$, $R^2$ and $R^3$ have the meanings defined hereinbefore.

A suitable organometallic catalyst is, for example, any agent known in the art for such a coupling reaction. Thus, for example, a suitable reagent is formed when, for example, bis(triphenylphosphine)palladium chloride or tetrakis(triphenylphosphine)palladium, and a copper halide, for example cuprous iodide, are mixed. The coupling is generally carried out in a suitable inert solvent or diluent, for example acetonitrile, 1,2-dimethoxyethane, toluene or tetrahydrofuran, at a temperature in the range, for example, 10° to 80° C., conveniently at or near 70° C., and in the presence of a suitable base such as, for example, a tri-(1-4C)alkylamine such as triethylamine, or a cyclic amine such as piperidine.

The ethynyl compound of the formula VI, used as a starting material, may be obtained, for example, by the alkylation, in the presence of a suitable base, of a compound of the formula II, wherein X, Ar, $R^1$, $R^2$ and $R^3$ have the meanings defined hereinbefore, with an alkylating agent of the formula H—C≡C—$A^1$—Z, wherein $A^1$ has the meaning defined hereinbefore and Z is a halogeno group, and provided that any amino, alkylamino, carboxy or hydroxy group in Ar, $R^1$, $R^2$ or $R^3$ is protected by a conventional protecting group.

(d) For the production of those compounds of the formula I wherein Ar bears an alkylsulphinyl or alkylsulphonyl substituent, wherein X is a sulphinyl or sulphonyl group, or wherein $R^2$ and $R^3$ together form a (3-6C)alkylene group which bears one or two alkylsulphinyl or alkylsulphonyl groups, the oxidation of a compound of the formula I wherein Ar bears an alkylthio substituent or wherein $R^2$ and $R^3$ together form a (3-6C)alkylene group which bears one or two alkylthio groups.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or t-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(e) For the production of those compounds of the formula I wherein Ar bears an alkanoylamino substituent, the acylation of a compound of the formula I wherein Ar bears an amino substituent.

A suitable acylating agent is, for example, any agent known in the art for the acylation of amino to acylamino, for example an acyl halide, for example a (2-6C)alkanoyl chloride or bromide, in the presence of a suitable base, an alkanoic acid anhydride, for example a (2-6C)alkanoic acid anhydride, or an alkanoic acid mixed anhydride, for example the mixed anhydride formed by the reaction of an alkanoic acid and a (1-4C)alkoxycarbonyl halide, for example a (1-4C)alkoxycarbonyl chloride, in the presence of a suitable base. In general the reaction is carried out in a suitable solvent or diluent such as methylene chloride, acetone, tetrahydrofuran or t-butyl methyl ether and at a temperature, for example, at or near ambient temperature, that is in the range 15° to 35° C. A suitable base when it is required is, for example, pyridine, 4-dimethylaminopyridine, triethylamine, ethyldiisopropylamine, N-methylmorpholine, an alkali metal carbonate, for example potassium carbonate, or an alkali metal carboxylate, for example sodium acetate.

(f) For the production of those compounds of the formula I wherein $R^1$ is alkanoyl or benzoyl optionally bearing a substituent as defined hereinbefore, the acylation of a compound of the formula I wherein $R^1$ is hydrogen. For the production of those compounds of the formula I wherein $R^1$ is alkanoyl the acylation reaction may be carried out using, for example, a suitable acylating agent as defined hereinbefore. For the production of those compounds of the formula I wherein $R^1$ is benzoyl optionally bearing a substituent the acylation may be carried out using, for example, a benzoyl halide, for example a benzoyl chloride or bromide, in the presence of a suitable base as defined hereinbefore.

(g) For the production of those compounds of the formula I wherein A is alkenylene, $R^1$ is alkenyl, the reduction of the corresponding compound wherein A is alkynylene or $R^1$ is alkynyl.

In general conditions which are standard in the art for the reduction of an alkynyl or alkynylene group are used. Thus, for example, the reduction may be carried out by the hydrogenation of a solution of the alkynyl or alkynylene compound in an inert solvent or diluent in the presence of a suitable metal catalyst. A suitable inert solvent is, for example, an alcohol, for example methanol or ethanol, or an ether, for example tetrahydrofuran or t-butyl methyl ether. A suitable metal catalyst is, for example, palladium or platinum on an inert support, for example charcoal or barium sulphate. Preferably a palladium-on-barium sulphate catalyst is used to substantially prevent over-reduction of the alkynyl or alkynylene group to an alkyl or alkylene group respectively. The reaction is generally carried out at a temperature at or near ambient temperature, that is in the range 15° to 35° C.

Alternatively the reduction may be carried out by treating a solution of the alkynyl or alkynylene compound in an inert solvent or diluent with a suitable mixture such as a 1:1 mixture of an organometallic hydride, for example a di-(1-6C)alkylaluminium hydride such as diisobutylaluminium hydride, and an alkyl metal, for example a (1-6C)alkyl lithium such as methyl lithium. A suitable inert solvent or diluent is, for example, tetrahydrofuran, diethyl ether or t-butyl methyl ether and, in general, the reaction is carried out at a temperature, for example, in the range −25° C. to ambient temperature (especially −10° to 10° C.).

(h) For the production of those compounds of the formula I wherein Q bears an alkyl or substituted alkyl substituent on an available nitrogen atom, or wherein Ar bears an alkoxy or substituted alkoxy substituent, the alkylation of a compound of the formula I wherein Q bears a hydrogen atom on said available nitrogen atom, or wherein Ar bears a hydroxy substituent.

A suitable alkylating agent is, for example, any agent known in the art for the alkylation of an available nitrogen atom, or of hydroxy to alkoxy or substituted alkoxy, for example an alkyl or substituted alkyl halide, for example a (1-6C)alkyl chloride, bromide or iodide or a substituted (1-4C)alkyl chloride, bromide or iodide, in the presence of a suitable base. A suitable base for the alkylation reaction is, for example, an alkali or alkaline earth metal carbonate, hydroxide or hydride, for example sodium carbonate, potassium carbonate, sodium hydroxide, potassium hydroxide, sodium hydride or potassium hydride. The alkylation reaction is preferably performed in a suitable inert solvent or diluent, for example, N,N-dimethylformamide, dimethylsulphoxide, acetone, 1,2-dimethoxyethane or tetrahydrofuran, and at a temperature in the range, for example, 10° to 150° C., conveniently at or near ambient temperature.

(i) For the production of those compounds of the formula wherein Q or Ar bears an amino substituent, the reduction of a compound of the formula I wherein Q or Ar bears a nitro substituent.

A suitable reducing agent is, for example, any agent known in the art for the reduction of a nitro group to an amino group. Thus, for example, the reduction may be carried out by the hydrogenation of a solution of the nitro compound in an inert solvent or diluent in the presence of a suitable metal catalyst, for example finely divided platinum metal (obtained by the reduction of platinum oxide in situ). A suitable inert solvent or diluent is, for example, an alcohol, for example methanol, ethanol or isopropanol, or an ether, for example tetrahydrofuran.

A further suitable reducing agent is, for example an activated metal such as activated iron (produced by washing iron powder with a dilute solution of an acid such as hydrochloric acid). Thus, for example, the reduction may be carried out by heating a mixture of the nitro compound and the activated metal in a suitable solvent or diluent such as a mixture of water an alcohol, for example, methanol or ethanol, to a temperature in the range, for example, 50° to 150° C., conveniently at or near 70° C.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

Many of the intermediates defined herein are novel, for example those of the formula V, and these are provided as a further feature of the invention.

As stated previously, the heterocyclic cycloalkanes of the formula I are inhibitors of the enzyme 5-LO. The effects of this inhibition may be demonstrated using one or more of the standard procedures set out below:

a) An in vitro spectrophotometric enzyme assay system, which assesses the inhibitory properties of a test compound in a cell free system using 5-LO isolated from guinea pig neutrophils and as described by D. Aharony and R. L. Stein (*J. Biol. Chem.*, 1986, 261(25), 11512-11519). This test provides a measure of the intrinsic inhibitory properties against soluble 5-LO in an extracellular environment.

b) An in vitro assay system involving incubating a test compound with heparinised human blood, prior to challenge with the calcium ionophore A23187 and then indirectly measuring the inhibitory effects on 5-LO by assaying the amount of LTB$_4$ using the specific radioimmunoassay described by Carey and Forder (F. Carey and R. A. Forder, *Brit. J. Pharmacol.* 1985, 84, 34P) which involves the use of a protein-LTB$_4$ conjugate produced using the procedure of Young et alia (*Prostaglandins,* 1983, 26(4), 605-613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane B$_2$(TxB$_2$) described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

c) An ex vivo assay system, which is a variation of test b) above, involving administration of a test compound (usually orally as the suspension produced when a solution of the test compound in dimethylsulphoxide is added to carboxymethylcellulose), blood collection, heparinisation, challenge with A23187 and radioimmunoassay of LTB$_4$ and TxB$_2$. This test provides an indication of the bioavailability of a test compound as an inhibitor of 5-LO or cyclooxygenase.

d) An in vitro assay system involving the measurement of the inhibitory properties of a test compound against the liberation of LTC$_4$ and PGE$_2$ induced by zymosan on mouse resident peritoneal macrophages, using the procedure of Humes (J. L. Humes et alia, *Biochem. Pharmacol.*, 1983, 32, 2319-2322) and conventional radioimmunoassay systems to measure LTC$_4$ and PGE$_2$. This test provides an indication of inhibitory effects against 5-LO and cyclooxygenase in a non-proteinaceous system.

e) An in vivo system involving the measurement of the effects of a test compound in inhibiting the inflammatory response to arachidonic aid in the rabbit skin model developed by D. Aked et alia (*Brit. J. Pharmacol.,* 1986, 89, 431-438). This test provides an in vivo model for 5-LO inhibitors administered topically or orally.

f) An in vivo system involving measuring the effects of a test compound administered orally or intravenously on a leukotriene dependent bronchoconstriction induced by an antigen challenge in guinea pigs pre-dosed with an antihistamine (mepyramine), a beta-adrenergic blocking agent (propranolol) and a cyclooxygenase inhibitor (indomethacin), using the procedure of W. H. Anderson et alia (*British J Pharmacology,* 1983, 78(1), 67-574). This test provides a further in vivo test for detecting 5-LO inhibitors.

Although the pharmacological properties of the compounds of the formula I vary with structural changes as expected, in general compounds of the formula I possess 5-LO inhibitory effects at the following concentrations or doses in one or more of the above tests a)-f):

Test a): IC$_{50}$ in the range, for example, 0.01-30 micromolar;

Test b): IC$_{50}$ (LTB$_4$) in the range, for example, 0.01-40 micromolar, IC$_{50}$ (TxB$_2$) in the range, for example, 40-200 micromolar;

Test c): oral ED$_{50}$(LTB$_4$) in the range, for example, 1-200 mg/kg;

Test d): IC$_{50}$ (LTC$_4$) in the range, for example, 0.001-1 micromolar, IC$_{50}$ (PGE$_2$) in the range, for example, 20-1000 micromolar;

Test e): inhibition of inflammation in the range, for example, 0.3-100 micrograms intradermally;

Test f): ED$_{50}$ in the range, for example, 0.5-10 mg/kg i.v.

No overt toxicity or other untoward effects are present in tests c), e) and/or f) when compounds of the formula I are administered at several multiples of their minimum inhibitory dose or concentration.

Thus, by way of example, the compound trans-1,2-dimethoxy-1-[3-(3-(2-pyridyl)prop-2-yn-1-yloxy)-phenyl]cyclopentane has an IC$_{50}$ of 8.0 $\mu$M against LTB$_4$ and of >40 micromolar against TxB$_2$ in test b), and an oral ED$_{50}$ of <100 mg/kg against LTB$_4$ in test c). In general those compounds of the formula I which are particularly preferred have an IC$_{50}$ of <1 micromolar against LTB$_4$ and of >40 micromolar against TxB$_2$ in test b), and an oral ED$_{50}$ of <100 mg/kg against LTB$_4$ in test c).

These compounds are examples of heterocyclic cycloalkanes of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises a heterocyclic cycloalkane of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a heterocyclic cycloalkane of the formula I or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to further feature of the invention there is provided a heterocyclic cycloalkane of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a cycloalkane of the formula I will naturally vary according to the nature and severity of the conditions, the age and sex of the animal or patient and the route of administration, according to well known principles of medicine. As mentioned above, heterocyclic cycloalkanes of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicyclic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises a heterocyclic cycloalkane of the formula I, or a pharmaceutically-acceptable salt thereof as defined hereinbefore, in conjunction or admixture with a cyclooxygenase inhibitory non-steroidal anti-inflammatory agent (such as mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The compounds of the formula I may also be used in combination with leukotriene antagonists such as those disclosed in European Patent Specifications Nos. 179619, 199543, 220066, 227241, 242167, 290145, 337765, 337766 and 337767, which are incorporated herein by way of reference.

The invention will now be illustrated in the following non-limiting Examples in which, unless otherwise stated:

(i) evaporations were carried out by rotary evaporations in vacuo and work-up procedures were carried out after removal of residual solids by filtration;

(ii) operations were carried out at room temperature, that is in the range 18°–20° and under an atmosphere of an inert gas such as argon;

(iii) column chromatography (by the flash procedure) and medium pressure liquid chromatography (MPLC) were performed on Merck Kieselgel silica (Art. 9385) obtained from E. Meck, Darmstadt, W. Germany;

(iv) yields are given for illustration only and are not necessarily the maximum attainable;

(v) the end-products of the formula I have satisfactory microanalyses and their structures were confirmed by NMR and mass spectral techniques;

(vi) intermediates were not generally fully characterised and purity was assessed by thin layer chromatographic, infra-red (IR) or NMR analysis; and (vii) melting points are uncorrected and were determined using a Mettler SP62 automatic melting point apparatus or an oil-bath apparatus; melting points for the end-products of the formula I were determined after recrystallisation from a conventional organic solvent such as ethanol, methanol, acetone, ether or hexane, alone or in admixture.

EXAMPLE 1

A mixture of 3-bromomethyl-1,2-dihydroquinolin-2-one (0.512 g, Chem. Pharm. Bull., 1985, 33, 3775), 1-(3-hydroxyphenyl)-trans-1,2-dimethoxycyclopentane (0.37 g), potassium carbonate (0.274 g) and dimethylformamide (3 ml) was stirred at ambient temperature for 15 hours. The mixture was partitioned between methylene chloride and water. The organic layer was washed with a saturated aqueous sodium chloride solution, dried (MgSO$_4$) and evaporated. The residue was purified by column chromatography using a 1:1 v/v mixture of toluene and ethyl acetate as eluent. There was thus obtained 1-[3-(1,2-dihydro-2-oxoquinolin-3-ylmethoxy)-phenyl]-trans-1,2-dimethoxycyclopentane (0.53 g, 86%), m.p. 100°-102° C.

The 1-(3-hydroxyphenyl)-trans-1,2-dimethoxycyclopentane, used as a starting material, was obtained as follows:

3-Methoxymethoxyphenyl bromide was prepared by the reaction of 3-bromophenol and dimethoxymethane using the general procedure described in *Synthesis*, 1976, 244. A Grignard reagent was prepared by heating a mixture of 3-methoxymethoxyphenyl bromide (5 g), magnesium (0.55 g) and tetrahydrofuran (20 ml) to 30° C. for 2 hours. The reagent was cooled to ambient temperature and a solution of 2-methoxycyclopentanone (2.5 g; *Bull. Soc. Chim. France*, 1973, 1417) in tetrahydrofuran (8 ml) was added dropwise. The mixture was stirred at ambient temperature for 15 hours and evaporated. The residue was partitioned between ethyl acetate and water. The organic layer was washed with a saturated aqueous sodium chloride solution, dried (MgSO4) and evaporated. The residue was purified by column chromatography using initially methylene chloride and then increasingly polar mixtures of methylene chloride and diethyl ether, up to a 1:1 v/v mixture, as eluent. There was thus obtained 1-hydroxy-2-methoxy-1-(3-methoxymethoxyphenyl)cyclopentane (3.11 g, 56%), as an oil.

A mixture of the product so obtained, sodium hydride (55% w/w dispersion in mineral oil, 1 g) and dimethylformamide (70 ml) was stirred at ambient temperature for 15 minutes. Methyl iodide (2 ml) and 1,4,7,10,13-pentaoxacyclopentadecane (hereinafter 15-crown-5, 0.1 g) were added and the mixture was stirred at ambient temperature for 15 hours. The mixture was evaporated and the residue was partitioned between methylene chloride and water. The organic layer was separated, washed with water, dried (MgSO4) and evaporated. There was thus obtained a mixture of diastereoisomers of 1,2-dimethoxy-1-(3-methoxymethoxyphenyl)cyclopentane from which the less polar isomer, trans-1,2-dimethoxy-1-(3-methoxymethoxyphenyl)cyclopentane (0.9 g, 47%) was obtained by column chromatography using a 49:1 v/v mixture of methylene chloride and diethyl ether as eluent.

A mixture of the trans-isomer so obtained (0.515 g), concentrated hydrochloric acid (0.1 ml), isopropanol (1 ml) and tetrahydrofuran (5 ml) was stirred at ambient temperature for 15 hours. The mixture was evaporated and the residue was partitioned between ethyl acetate and water. The organic layer was washed with a saturated aqueous sodium chloride solution, dried (MgSO4) and evaporated. The residue was purified by column chromatography using a 9:1 v/v mixture of methylene chloride and diethyl ether as eluent. There was thus obtained 1-(3-hydroxyphenyl)-trans-1,2-dimethoxycyclopentane (0.24 g, 57%), m.p. 73°-74° C.

EXAMPLE 2

The procedure described in Example 1 was repeated except that 3-(2-pyridyl)prop-2-yn-1-yl bromide hydrobromide was used in place of 3-bromomethyl-1,2-dihydroquinolin-2-one. There was thus obtained trans-1,2-dimethoxy-1-[3-(3-(2-pyridyl)prop-2-yn-1-yloxy)-phenyl]cyclopentane as an oil in 72% yield.

NMR Spectrum: (CDCl3, delta values) 1.56-2.26(m, 6H), 2.96(s, 3H), 2.97(s, 3H), 3.6(d, 1H), 4.94(s, 2H), 6.99-7.64(m, 7H), 8.59(d, 1H).

3-(2-Pyridyl)prop-2-yn-1-yl bromide hydrobromide used as a starting material was obtained as follows:

2-Propynyl alcohol (35 ml) was added dropwise to a stirred mixture of 2-bromopyridine (13.7 g), bis(triphenylphosphine)palladium chloride (1.54 g), triethylamine (21 ml), cuprous iodide (1.5 g) and acetonitrile (150 ml) and the mixture was stirred at ambient temperature for 30 minutes and then heated to 60° C. for 2 hours. The mixture was cooled to ambient temperature, poured into water (200 ml) and neutralised by adding dilute aqueous hydrochloric acid. The mixture was extracted with methylene chloride (2×500 ml) and the combined extracts were washed with water (500 ml), dried (MgSO4) and evaporated. The residue was purified by column chromatography eluting with a 1:1 v/v mixture of methylene chloride and ethyl acetate to give 3-(2-pyridyl)prop-2-yn-1-yl alcohol (14 g, 70%), m.p. 78°-80° C. (recrystallised from a mixture of hexane and ethyl acetate).

A solution of bromine (3.1 ml) in methylene chloride (3 ml) was added to a mixture of triphenylphosphine (10.1 g) and methylene chloride (72 ml) which had been cooled to −8° C. in a salted ice-bath. A solution of the alcohol (4.8 g) obtained immediately above in methylene chloride (36 ml) was added and the mixture was stirred for 10 minutes and cooled to approximately −10° C. The mixture was filtered to give 3-(2-pyridyl)-prop-2-yn-1-yl bromide hydrobromide (5.8 g, 58%), m.p. 112°-114° C., which was used without further purification.

EXAMPLE 3

Using the procedure described in Example 1, 3-(2-pyridyl)prop-2-yn-1-yl bromide hydrobromide was reacted with (1RS,2SR)-1-(5-fluoro-3-hydroxyphenyl)-1,2-dimethoxycyclopentane to give (1RS,2SR)-1-[5-fluoro-3-(3-(2-pyridyl)prop-2-yn-1-yloxy)phenyl]-1,2-dimethoxycyclopentane in 83% yield, as an oil.

NMR Spectrum (CDCl3, delta values) 1.6-2.25(m, 6H), 2.94(s, 3H), 2.97(s, 3H), 3.55(m, 1H), 5.21(s, 2H), 6.55-8.0(m, 10H).

The (1RS,2SR)-1-(5-fluoro-3-hydroxyphenyl)-1,2-dimethoxycyclopentane, used as a starting material, was obtained as follows:

Benzyl alcohol (1.0 g) was added to a suspension of sodium hydride (60% w/w dispersion in mineral oil, 0.48 g) in dimethylacetamide (15 ml) and the mixture was stirred at ambient temperature for 5 minutes. The mixture was cooled in an ice-bath and 3,5-difluorobromobenzene (1.15 ml) was added. The mixture was stirred at ambient temperature for 30 minutes and then partitioned between diethyl ether and water. The organic phase was washed with water, dried (MgSO4) and evaporated. The residue was purified by column chromatography using methylene chloride as eluent. There was thus obtained 3-benzyloxy-5-fluorobromobenzene (2.34 g, 83%), as an oil.

After repetition of the above reaction, a solution of 2-methoxycyclopentanone (12.5 g) in tetrahydrofuran (10 ml) was added to a solution of 3-benzyloxy-5-fluorophenylmagnesium bromide [prepared by heating a mixture of 3-benzyloxy-5-fluorobromobenzene (31 g), magnesium powder (2.65 g) and tetrahydrofuran (20 ml) to 40° C. for 2 hours] and the mixture was stirred at ambient temperature for 2 hours. The mixture was evaporated and the residue was partitioned between diethyl ether and water. The organic layer was washed with water, dried (MgSO4) and evaporated. The residue was purified by column chromatography using a 9:1 v/v mixture of methylene chloride and diethyl ether as eluent. There was thus obtained, as a mixture of diastereoisomers, 1-(3-benzyloxy-5-fluorophenyl)-2-methoxycyclopentanol (21.7 g, 62%), as an oil.

Using the procedure described in the second paragraph of the portion of Example 1 which is concerned with the preparation of starting materials, a portion (18.2 g) of the product so obtained was reacted with methyl iodide to give, as a mixture of diastereoisomers, 1-(3-benzyloxy-5-fluorophenyl)-1,2-dimethoxycyclopentane. The diastereoisomers were separated by column chromatography using a 49:1 v/v mixture of methylene chloride and diethyl ether as eluent. There was thus obtained in pure form the diastereoisomer wherein the methoxy groups are in the trans-relationship i.e. (1RS,2SR)-1-(3-benzyloxy-5-fluorophenyl)-1,2-dimethoxycyclopentane (12.7 g, 67%).

A mixture of a portion (6.5 g) of the compound so obtained, 10% palladium-on-charcoal catalyst (0.65 g) and ethanol (100 ml) was stirred under an atmosphere of hydrogen for 3 hours. The mixture was filtered and the filtrate was evaporated. There was thus obtained the required starting material (4.58 g, 95%), m.p. 94°-95° C.

EXAMPLE 4

Using the procedure described in Example 1, the appropriate alkyl bromide was reacted with the appropriate cyclopentanol to give the compounds described in the following table:

TABLE I

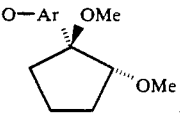

Q—CH₂—O—Ar   OMe

| Ex. 4 Compd. No. | Q | Ar | Yield (%) | m.p. (°C.) |
| --- | --- | --- | --- | --- |
| 1<sup>a</sup> | 6-quinoxalinyl | 5-fluoro-1,3-phenylene | 75 | 60-61 |
| 2<sup>b</sup> | 1,2-dihydro-1-methyl-2-oxoquinolin-6-yl | 5-fluoro-1,3-phenylene | 57 | 85 |
| 3<sup>c</sup> | 1,2-dihydro-1-methyl-2-oxoquinolin-5-yl | 5-fluoro-1,3-phenylene | 75 | 137-139 |
| 4<sup>d</sup> | 1,2-dihydro-1-methyl-2-oxoquinolin-7-yl | 5-fluoro-1,3-phenylene | 76 | 116-118 |
| 5<sup>e</sup> | 1,2-dihydro-1-(2-fluoroethyl)-2-oxoquinolin-6-yl | 5-fluoro-1,3-phenylene | 61 | 109-112 |
| 6<sup>f</sup> | 1,2-dihydro-1-ethyl-2-oxoquinolin-6-yl | 5-fluoro-1,3-phenylene | 59 | 115-116 |

Notes a. 6-Bromomethylquinoxaline, used as the alkylating agent, is described in *J. Het. Chem.*, 1974, 11, 595.

b. The 6-bromomethyl-1,2-dihydro-1-methylquinolin-2-one, used as a starting material, was obtained as follows:

A mixture of 1,2-dihydro-1,6-dimethylquinolin-2-one (4.4 g; *Helv. Chim. Acta*, 1970, 53, 1903), N-bromosuccinimide (4.53 g), azobisisobutyronitrile (0.01 g) and carbon tetrachloride (75 ml) was heated to reflux for 3 hours and illuminated with the light from a 275 watt lamp. The mixture was evaporated and the residue was partitioned between ethyl acetate and water. The organic phase was washed with water, dried (MgSO₄) and evaporated. The residue was purified by column chromatography using a 2:1 v/v mixture of toluene and ethyl acetate as eluent. There was thus obtained the required starting material (4.8 g, 75%), as a solid, m.p. 108°-108° C.

NMR Spectrum (CDCl₃, delta values) 3.7(s, 3H), 4.57(s, 2H), 6.7-7.5(d, 1H), 7.25-7.65(m, 4H).

c. The 5-bromomethyl-1,2-dihydro-1-methylquinolin-2-one, used as a starting material, was obtained as follows:

1,2-Dihydro-5-methylquinolin-2-one (1.59 g; *Synthesis*, 1975, 739) was added to a stirred suspension of sodium hydride (55% w/w dispersion in mineral oil, 0.264 g) in dimethylformamide (40 ml) and the mixture was heated to 50° C. for 45 minutes. The mixture was cooled to 0° C. and methyl iodide (0.93 ml) was added dropwise. The mixture was stirred at ambient temperature for 16 hours. The mixture was evaporated and the residue was partitioned between ethyl acetate and water. The organic phase was washed with a saturated aqueous sodium chloride solution, dried (MgSO₄) and evaporated. The residue was purified by column chromatography using a 19:1 v/v mixture of methylene chloride and methanol as eluent. There was thus obtained 1,2-dihydro-1,5-dimethylquinolin-1-one (1.5 g, 87%), m.p. 107°-108° C.

A mixture of a portion (1.21 g) of the product so obtained, N-bromosuccinimide (1.37 g), benzoyl peroxide (0.035 g) and carbon tetrachloride (25 ml) was heated to reflux for 40 minutes and irradiated with the light from a 275 watt lamp. The mixture was evaporated and the residue was partitioned between ethyl acetate and water. The organic phase was washed with a saturated aqueous sodium chloride solution, dried (MgSO₄) and evaporated. The residue was purified by column chromatography using in turn methylene chloride and then a 4:1 v/v mixture of toluene and ethyl acetate as eluent. There was thus obtained the required starting material (1.09 g, 59%), m.p. 169° C.

d. The 7-bromomethyl-1,2-dihydro-1-methylquinolin-2-one, used as a starting material, was obtained using the following procedure:

1,2-Dihydro-7-methylquinolin-2-one (*Synthesis*, 1975, 739) was reacted with methyl iodide using the procedure described in Note c. immediately above. There was thus obtained 1,2-dihydro-1,7-dimethylquinolin-2-one in 79% yield, m.p. 111°-112° C.

The product so obtained was brominated using the procedure described in Note c. immediately above to give the required starting material in 57% yield, m.p. 170° C.

e. The 6-bromomethyl-1,2-dihydro-1-(2-fluoroethyl)-quinolin-2-one, used as the alkylating agent, was obtained from 1,2-dihydro-6-methylquinolin-2-one using the procedures described in Note c. immediately above, except that 2-fluoroethyl bromide was used in place of methyl iodide. There was thus obtained the required starting material in 48% yield, as a solid.

NMR Spectrum (CDCl₃, delta values) 4.56(s, 2H), 4.5-4.9(m, 4H), 6.72(d, 1H), 7.3-7.8(m, 4H)

f. The 6-bromomethyl-1,2-dihydro-1-ethylquinolin-2-one, used as a starting material, was obtained from 1,2-dihydro-6-methylquinolin-2-one using the procedures described in Note c. immediately above except that ethyl iodide was used in place of methyl iodide. There was thus obtained the required starting material in 21% yield, as an oil.

NMR Spectrum (CDCl₃, delta values) 1.38(t, 3H), 4.35(q, 2H), 4.57(s, 2H), 6.72(d, 1H), 7.63(d, 1H), 7.1-7.6(m, 3H).

EXAMPLE 5

The following illustrate representative pharmaceutical dosage forms containing the compound of formula I, or a pharmaceutically-acceptable salt salt thereof (hereafter compound X), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |
| (b) Tablet II | mg/tablet |
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c) Tablet III | mg/tablet |
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |
| (d) Capsule | mg/capsule |
| Compound X | 10 mg |
| Lactose Ph.Eur | 488.5 |
| Magnesium stearate | 1.5 |
| (e) Injection I | (50 mg/ml) |
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |
| (f) Injection II | (10 mg/ml) |
| Compound X | 1.0% w/v |
| Sodium phosphate BP | 3.6% w/v |
| 0.1M Sodium hydroxide solution | 15.0% v/v |
| Water for injection to 100% | |
| (g) Injection III | (1 mg/ml, buffered to pH 6) |
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |
| (h) Aerosol I | mg/ml |
| Compound X | 10.0 |
| Sorbitan trioleate | 13.5 |
| Trichlorofluoromethane | 910.0 |
| Dichlorodifluoromethane | 490.0 |
| (i) Aerosol II | mg/ml |
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |
| (j) Aerosol III | mg/ml |
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |
| (k) Aerosol IV | mg/ml |
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

Note

The above formulations may be obtained by conventional procedures well known in the pharmaceutical art. The tablets (a)-(c) may be enteric coated by conventional means, for example to provide a coating of cellulose acetate phthalate. The aerosol formulations (h)-(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

CHEMICAL FORMULAE

I

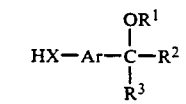

II

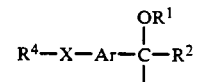

III

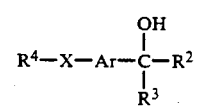

IV

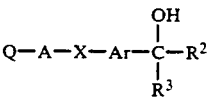

V

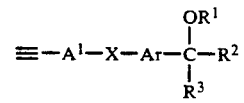

VI

What we claim is:

1. A heterocyclic cycloalkane of the formula I

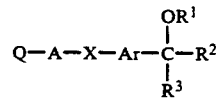

I wherein Q is quinolyl or hydrogenated derivative thereof which may optionally bear one, two or three substituents selected from halogeno, hydroxy, oxo, carboxy, cyano, amino, (1-4C)alkyl, (1-4C)alkoxy, fluoro-(1-4C)alkyl, (1-4C)alkylamino, di-[(1-4C)alkyl]amino, hydroxy-(1-4C)alkyl, amino-(1-4C)alkyl, (1-4C)alkylamino-(1-4C)alkyl, di-[(1-4C)alkyl]amino-(1-4C)alkyl, amino-(2-4C)alkoxy, (1-4C)alkylamino-(2-4C)alkoxy, di-[(1-4C)alkyl]amino-(2-4C)alkoxy and phenyl-(1-4C)alkyl;

wherein A is (1-6C)alkylene, (3-6C)alkenylene, (3-6C)alkynylene or cyclo(3-6C)alkylene;

wherein X is oxy, thio, sulphinyl, sulphonyl or imino;

wherein Ar is phenylene which may optionally bear one or two substituents selected from halogeno, hydroxy, amino, nitro, cyano, ureido, carbamoyl, (1–4C)alkyl, (3–4C)alkenyloxy, (1–4C)alkoxy, (1–4C)alkylthio, (1–4C)alkylsulphinyl, (1–4C)alkylsulphonyl, (1–4C)alkylamino, di-[(1–4C)alkyl]amino, fluoro-(1–4C)alkyl, (1–4C)alkoxycarbonyl, N-[(1–4C)alkyl]carbamoyl, N,N-di-[(1–4C)alkyl]carbamoyl, (2–4C)alkanoylamino, cyano-(1–4C)alkoxy, carbamoyl-(1–4C)alkoxy, amino-(2–4C)alkoxy, (1–4C)alkylamino-(2–4C)alkoxy, di-[(1–4C)alkyl]amino-(2–4C)alkoxy and (1–4C)alkoxycarbonyl-(1–4C)alkoxy;

wherein $R^1$ is hydrogen, (1–6C)alkyl, (3–6C)alkenyl, (3–6C)alkynyl, cyano-(1–4C)alkyl or (2–4C)alkanoyl, or $R^1$ is benzoyl which may optionally bear a substituent selected from halogeno, (1–4C)alkyl and (1–4C)alkoxy; and wherein $R^2$ and $R^3$ together form a (3–6C)alkylene group which, together with the carbon atom to which $R^2$ and $R^3$ are attached, defines a ring having 4 to 7 ring atoms, and which ring may bear one or two substituents, which may be the same or different, selected from hydroxy, (1–4C)alkyl, (1–4C)alkoxy, (1–4C)alkylthio, (1–4C)alkylsulphinyl and (1–4C)alkylsulphonyl, or which ring may bear a (1–4C)alkylenedioxy substituent;

or a pharmaceutically-acceptable salt thereof.

2. A heterocyclic cycloalkane of the formula I as claimed in claim 1 where Q is quinolyl or hydrogenated derivative thereof, which may optionally bear one, two or three substituents selected from fluoro, chloro, hydroxy, oxo, methyl, ethyl, propyl, trifluoromethyl, 2-fluoromethyl, 2-dimethylaminoethyl and benzyl;

where A is methylene, 1-propenylene or 1-propynylene;

wherein X is oxy;

wherein Ar is 1,3-phenylene or 1,4-phenylene which may optionally bear one or two substituents selected from fluoro, chloro, hydroxy, amino, ureido, methoxy and trifluoromethyl;

wherein $R^1$ is methyl, ethyl, allyl or 2-propynyl; and wherein $R^2$ and $R^3$ together form a tetramethylene or pentamethylene group which, together with the carbon atom to which $R^2$ and $R^3$ are attached, defines a ring having 5 or 6 ring atoms and which ring may bear a substituent selected from hydroxy, methyl, methoxy and ethoxy; or a pharmaceutically-acceptable salt thereof.

3. A heterocyclic cycloalkane of the formula I as claimed in claim 1 wherein Q is 2-quinolyl, 3-quinolyl, 6-quinolyl or 7-quinolyl or hydrogenated derivative thereof which may optionally bear one or two substituents selected from fluoro, chloro, hydroxy, oxo, cyano, methyl, methoxy and trifluoromethyl;

A is methylene, ethylene, trimethylene, 1-propenylene, 2-methylprop-1-enylene or 1-propynylene;

X is oxy;

Ar is 1,3-phenylene or 1,4-phenylene which may optionally bear one substituent selected from fluoro, chloro, hydroxy, amino, nitro, methyl, methoxy, methylthio, methylsulphinyl, methylsulphonyl, methylamino, dimethylamino, trifluoromethyl, acetamido, cyanomethoxy and carbamoylmethoxy;

$R^1$ is methyl, ethyl, allyl or 2-propynyl; and $R^2$ and $R^3$ together form a tetramethylene or pentamethylene group which, together with the carbon atom to which $R^2$ and $R^3$ are attached, defines a ring having 5 or 6 ring atoms and which ring may bear a substituent selected from hydroxy, methyl, methoxy, ethoxy, methylthio, methylsulphinyl, methylsulphonyl and methylenedioxy;

or a pharmaceutically-acceptable salt thereof.

4. A heterocyclic cycloalkane of the formula I as claimed in claim 1 wherein Q is 3-quinolyl, 5-quinolyl, 6-quinolyl or 7-quinolyl or hydrogenated derivative thereof which may optionally bear one or two substituents selected from hydroxy, oxo, methyl, ethyl, propyl, 2-fluoroethyl, 2-dimethylaminoethyl and benzyl;

wherein A is methylene, 1-propenylene or 1-propynylene;

wherein X is oxy;

wherein Ar is 1,3-phenylene or 1,4-phenylene which may optionally bear one to two substituents selected from fluoro, chloro, amino, methoxy and trifluoromethyl;

wherein $R^1$ is methyl, ethyl or allyl; and wherein $R^2$ and $R^3$ together form a tetramethylene group which, together with the carbon atom to which $R^2$ and $R^3$ are attached, defines a ring having 5 ring atoms and which ring may bear a substituent selected from hydroxy and methoxy; or a pharmaceutically-acceptable salt thereof.

5. A heterocyclic cycloalkane of the formula I as claimed in claim 1 wherein Q is 1,2-dihydro-2-oxoquinolin-3-yl, 1,2-dihydro-2-oxoquinolin-5-yl, 1,2-dihydro-2-oxoquinolin-6-yl or 1,2-dihydro-2-oxoquinolin-7-yl which bears a 1-substituent selected from methyl, ethyl and 2-fluoroethyl;

wherein A is methylene;

wherein X is oxy;

wherein Ar is 1,3-phenylene which may optionally bear one fluoro substituent;

wherein $R^1$ is methyl; and wherein $R^2$ and $R^3$ together form a tetramethylene group which, together with the carbon atom to which $R^2$ and $R^3$ are attached, defines a ring having 5 ring atoms and which ring bears a methoxy substituent; or a pharmaceutically-acceptable salt thereof.

6. A heterocyclic cycloalkane of the formula I as claimed in claim 1 wherein Q is 1,2-dihydro-1-methyl-2-oxoquinolin-3-yl;

A is methylene or 1-propynylene;

Ar is 1,3-phenylene or 5-fluoro-1,3-phenylene;

$R^1$ is methyl; and $R^2$ and $R^3$ together form a tetramethylene group, which, together with the carbon atom to which $R^2$ and $R^3$ are attached, defines a ring having 5 ring atoms and which ring bears a 2-methoxy substituent;

or a pharmaceutically-acceptable salt thereof.

7. A pharmaceutical composition which comprises a 5-lipoxygenase inhibitory amount of a heterocyclic cycloalkane of the formula I, or a pharmaceutically-acceptable salt thereof, as claimed in any one of claims 1 to 6 in association with a pharmaceutically-acceptable diluent or carrier.

8. A method of treating a disease or medical condition mediated alone or in part by one or more leukotrienes which comprises administering to a warm-blooded animal requiring such treatment an effective amount of a heterocyclic cycloalkane of the formula I, or a pharmaceutically-acceptable salt thereof, as claimed in any one of claims 1 to 7.

9. The heterocyclic compound (1RS,2SR)-1-[5-fluoro-3(1,2-dihydro-1-methyl-2-oxoquinolin-6-ylmethoxy)phenyl]-1,2-dimethoxycylopentane.

* * * * *